(12) United States Patent
Mougin

(10) Patent No.: US 12,050,229 B2
(45) Date of Patent: Jul. 30, 2024

(54) DEVICE AND METHOD FOR ANALYZING LIQUID COMPOSITIONS, PARTICULARLY SAMPLES OF LIQUIDS OF BIOLOGICAL ORIGIN PARTICULARLY FOR DETERMINING ELECTROLYTES

(71) Applicant: NEOVITEA, Saint Jean d'Illac (FR)

(72) Inventor: Gilles Mougin, Andrenos-les-Bains (FR)

(73) Assignee: NEOVITEA, Saint Jean d'Illac (FR)

( * ) Notice: Subject to any disclaimer, the term of this patent is extended or adjusted under 35 U.S.C. 154(b) by 1025 days.

(21) Appl. No.: 16/961,159

(22) PCT Filed: Dec. 11, 2018

(86) PCT No.: PCT/EP2018/084358
§ 371 (c)(1),
(2) Date: Jul. 9, 2020

(87) PCT Pub. No.: WO2019/115526
PCT Pub. Date: Jun. 20, 2019

(65) Prior Publication Data
US 2020/0363441 A1    Nov. 19, 2020

(30) Foreign Application Priority Data
Dec. 11, 2017  (FR) .................. 17 71340

(51) Int. Cl.
*G01N 35/04* (2006.01)
*G01N 33/49* (2006.01)
(Continued)

(52) U.S. Cl.
CPC ........ *G01N 35/04* (2013.01); *G01N 33/4915* (2013.01); *G01N 33/492* (2013.01);
(Continued)

(58) Field of Classification Search
CPC ................................... G01N 33/4915
See application file for complete search history.

(56) References Cited

U.S. PATENT DOCUMENTS 4,627,893 A    12/1986  Cormier et al.
4,649,028 A *  3/1987  Kaltenbach ........ G01N 35/1097
                                              137/625.13
(Continued)

FOREIGN PATENT DOCUMENTS

DE    3040168 A1     5/1981
EP    1939614 A2     7/2008
JP    H01295158 A    11/1989

OTHER PUBLICATIONS

International Search Report; priority document.

*Primary Examiner* — Kristina M Deherrera
*Assistant Examiner* — Mark A Shabman
(74) *Attorney, Agent, or Firm* — Greer Burns & Crain, Ltd.

(57) ABSTRACT

A device and method for analyzing samples of liquid compositions of biological origin, particularly whole blood samples for determining, in particular, electrolytes. The device includes a frame, a sampling module, an analysis module including electrodes, a liquid product reserve module, a control module including electronic and computing devices, as well as a network of fluid connections.

13 Claims, 5 Drawing Sheets

(51) Int. Cl.
    *G01N 35/00*     (2006.01)
    *G01N 35/10*     (2006.01)

(52) U.S. Cl.
    CPC ... *G01N 33/4925* (2013.01); *G01N 35/00623* (2013.01); *G01N 35/1095* (2013.01); *G01N 2035/0413* (2013.01)

(56) References Cited

U.S. PATENT DOCUMENTS

| | | | | |
|---|---|---|---|---|
| 4,871,439 | A * | 10/1989 | Enzer | G01N 27/4165 204/411 |
| 4,935,106 | A * | 6/1990 | Liston | G01N 27/3271 205/792 |
| 5,980,830 | A * | 11/1999 | Savage | G01N 33/4925 422/63 |
| 6,436,349 | B1 * | 8/2002 | Carey | G01N 35/021 422/549 |
| 8,017,094 | B2 * | 9/2011 | Meyer | B01F 31/275 422/561 |
| 2008/0135409 | A1 | 6/2008 | Sakuraoka et al. | |
| 2009/0156966 | A1 * | 6/2009 | Kontschieder | G01N 33/48771 600/584 |
| 2019/0353625 | A1 * | 11/2019 | Tomono | G01N 30/16 |

\* cited by examiner

DEVICE AND METHOD FOR ANALYZING LIQUID COMPOSITIONS, PARTICULARLY SAMPLES OF LIQUIDS OF BIOLOGICAL ORIGIN PARTICULARLY FOR DETERMINING ELECTROLYTES

CROSS-REFERENCES TO RELATED APPLICATIONS

This application claims the benefit of the International Application No. PCT/EP2018/084358, filed on Dec. 11, 2018, and of the French patent application No. 1771340 filed on Dec. 11, 2017, the entire disclosures of which are incorporated herein by way of reference.

FIELD OF THE INVENTION

The present invention relates to a device and a method for analyzing samples of liquids of biological origin, particularly whole blood samples for determining, in particular, electrolytes. It is known that measurements of electrolytes in the blood, in combination with other parameters, allow the practitioners involved to diagnose probable pathologies quickly and precisely.

BACKGROUND OF THE INVENTION

Analyses of this type are carried out in the laboratory using sophisticated devices requiring substantial investment, which is difficult to recoup without a very high demand and a very large number of daily analyses.

Outsourcing these operations requires both transferring samples and preserving them, as well as a turnaround time between sending out the sample and obtaining the results. In addition, sophisticated devices are expensive and not adaptable, that is to say, they offer the analysis of the main electrolytes and other parameters directly.

Biochemical analyzers are known, in particular marketed under the registered trademark COBAS, which allow for the automatic analysis of electrolytes in blood, plasma or other solutions thanks to an interchangeable module containing the suitable measurement devices. Such a device meets the need for in situ analyses, but the arrangement of this device remains complex and although choosing electrolytes is possible, it must, however, be done initially, when the device is configured. Parameters such as pH and calcium, for example, still cannot be implemented due to processing times.

Also known is US patent application 20090156966 which relates to a cassette with modules that contain memory storage means to link information to the cassette, to allow a recognition of the type of cassette by the device in which it is integrated, and to carry out the integration of the data into the control system directly, without intervention, through pre-programming.

There is a need for devices that have more modest dimensions, are adaptable, make it possible to obtain results in situ and thus with very quick processing times, are simple to handle, and allow traceability and analyses that are as precise as with sophisticated devices, at a price that allows for installation and use while limiting financial burdens. The possibility of an additional analysis of the CO2 level in the blood may also be a useful addition for this type of adaptable device.

BRIEF DESCRIPTION OF THE DRAWINGS

The device for analyzing samples of liquids of biological origin, according to the invention, for the determination in particular of electrolytes is now described in detail, according to a particular, non-limiting embodiment, the description being established with reference to the attached drawings.

DETAILED DESCRIPTION OF THE PREFERRED EMBODIMENTS

Figure 1:
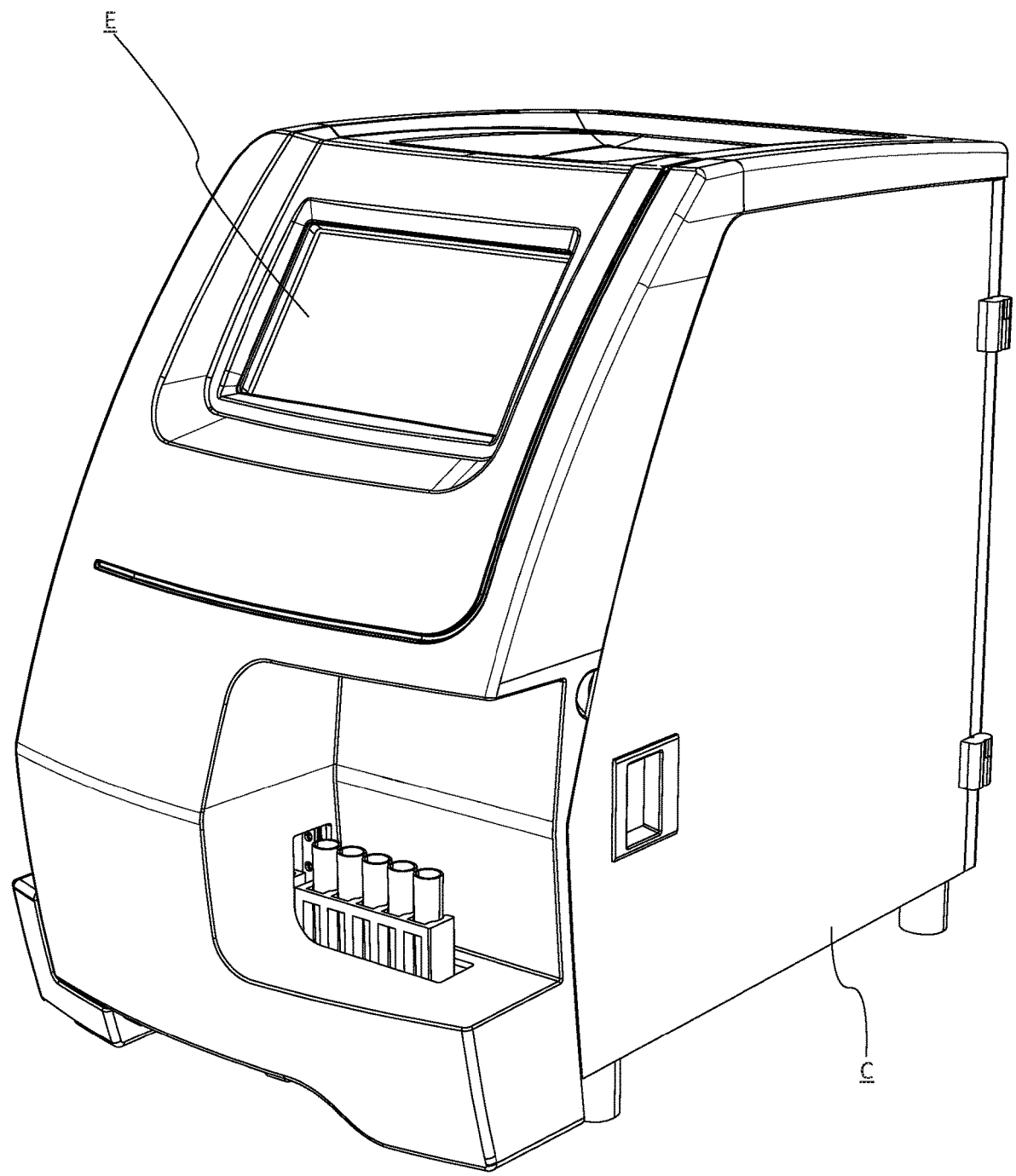
FIG. 1 shows a perspective view of the device according to the present invention, with its casing.
Figure 2:
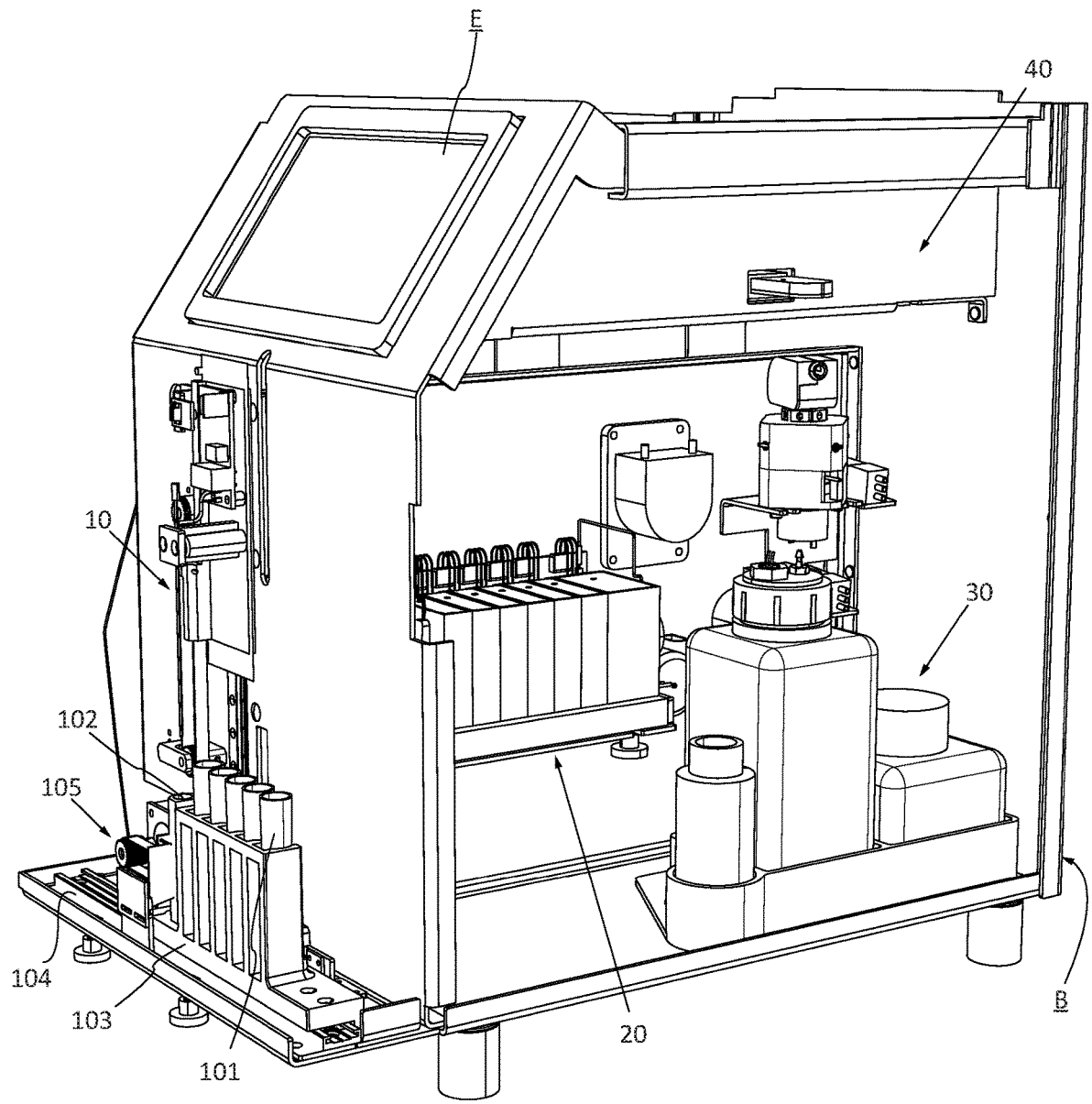
FIG. 2 shows a perspective view of the device in FIG. 1, with the casing removed.

The detailed description is based on the various figures, interchangeably.

The device for analyzing samples of liquid blood of biological origin according to the present invention comprises a frame B, a casing C with a display and dialog screen E on the front face, in this case a touchscreen, as well as a printer, not shown for clarity of the drawing. Standard known computer connections and networks are also provided.

The frame receives a sampling module 10, an analysis module 20 comprising electrodes, a liquid product reserve module 30, a control module 40 comprising electronic and computing means, as well as a network of fluid connections 50.

On the front face of the frame B, the module 10 for taking samples of liquid compositions comprises a tube support 100, holding sample tubes 101 for the samples, and a reference tube 102 provided with a tap 102P in the lower part. This tube support 100 is mounted to be movable in translation on a tube carriage 103, movable on guides 104.

The carriage 103 is linked to motor means 105, in this case an electric stepper motor 106, two pulleys 107 and 108, one of which is powered and driven by the motor, with a toothed belt 109 stretched between the two pulleys.

The carriage 103 is secured to the toothed belt so that when the belt moves in one direction or the other, the carriage is moved in the same way. The axis XX' passing through the centers of the two pulleys is horizontal, like the guides 104.

The translation of the tube carriage 103 thus obtained occurs in a plane parallel to the facade, the amplitude of the movements always leaving the carriage within the width of the facade. On this same front face of the frame B, the sampling module 10 further comprises sampling means 110 which themselves comprise a needle carriage 111 on which is disposed a sampling needle 112 with a central channel. The needle carriage 111 is mounted to be movable in translation on guides 113, the guides being oriented vertically along the axis YY', i.e. perpendicular to the axis XX'.

An arrangement of the same type as for the tube carriage 103 is realized in the form of a toothed belt 114 stretched between two pulleys 115, 116 of which the straight line joining the axes of rotation of the two the pulleys is oriented along the YY' axis. One of the pulleys, in this case the upper pulley 115, is rotated by an electric stepper motor 106', of the same type as the motor 106. The needle carriage 111 thus allows for up and down movement of the sampling needle 112 it carries.

The electrode module 20 comprises a rack 200 intended to receive electrodes 201 for analyzing electrolytes of type 201Ca, 201, 201Na, etc.

Figure 3:
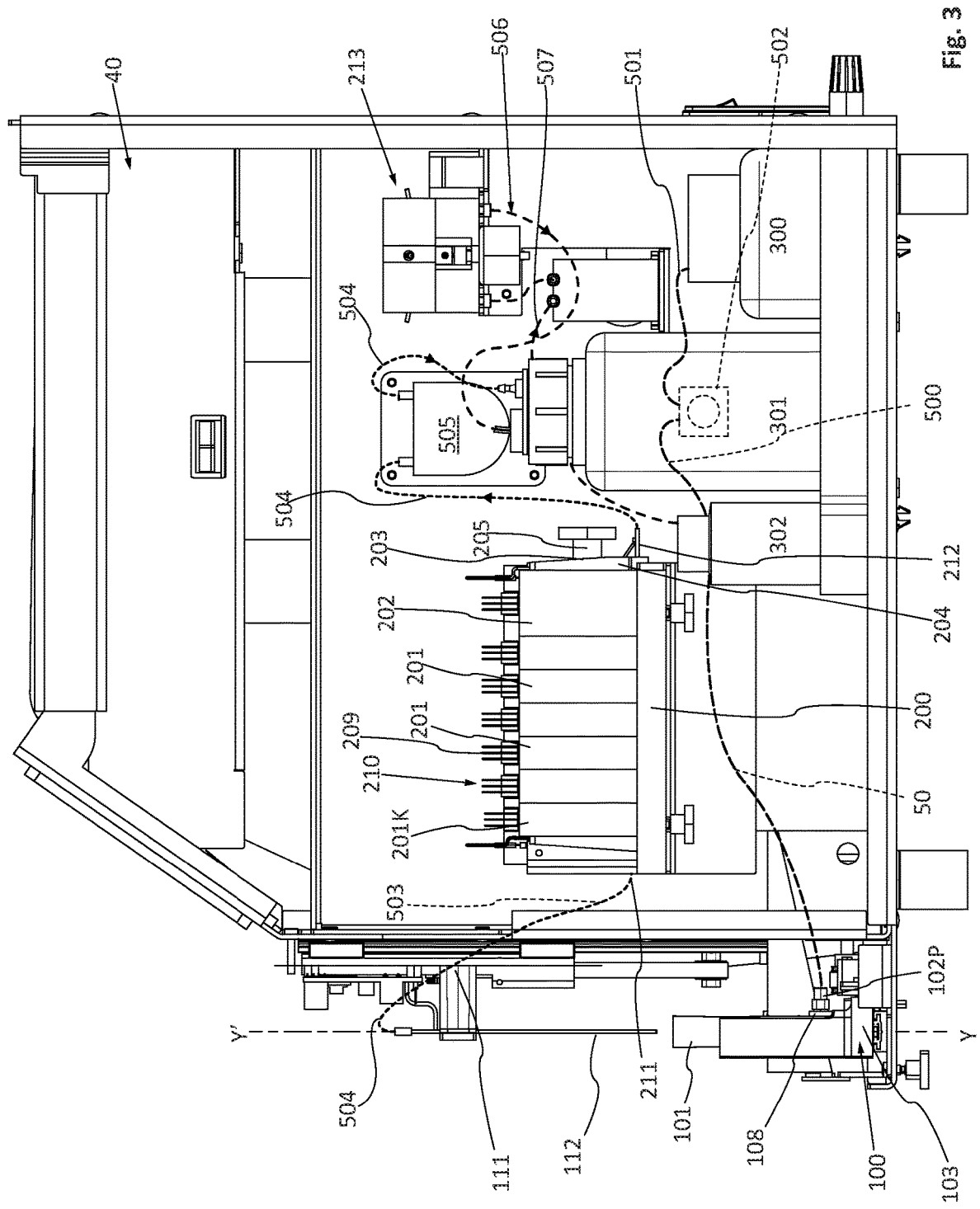
FIG. 3 shows a left side elevation view of the device in FIG. 2.
Figure 4:
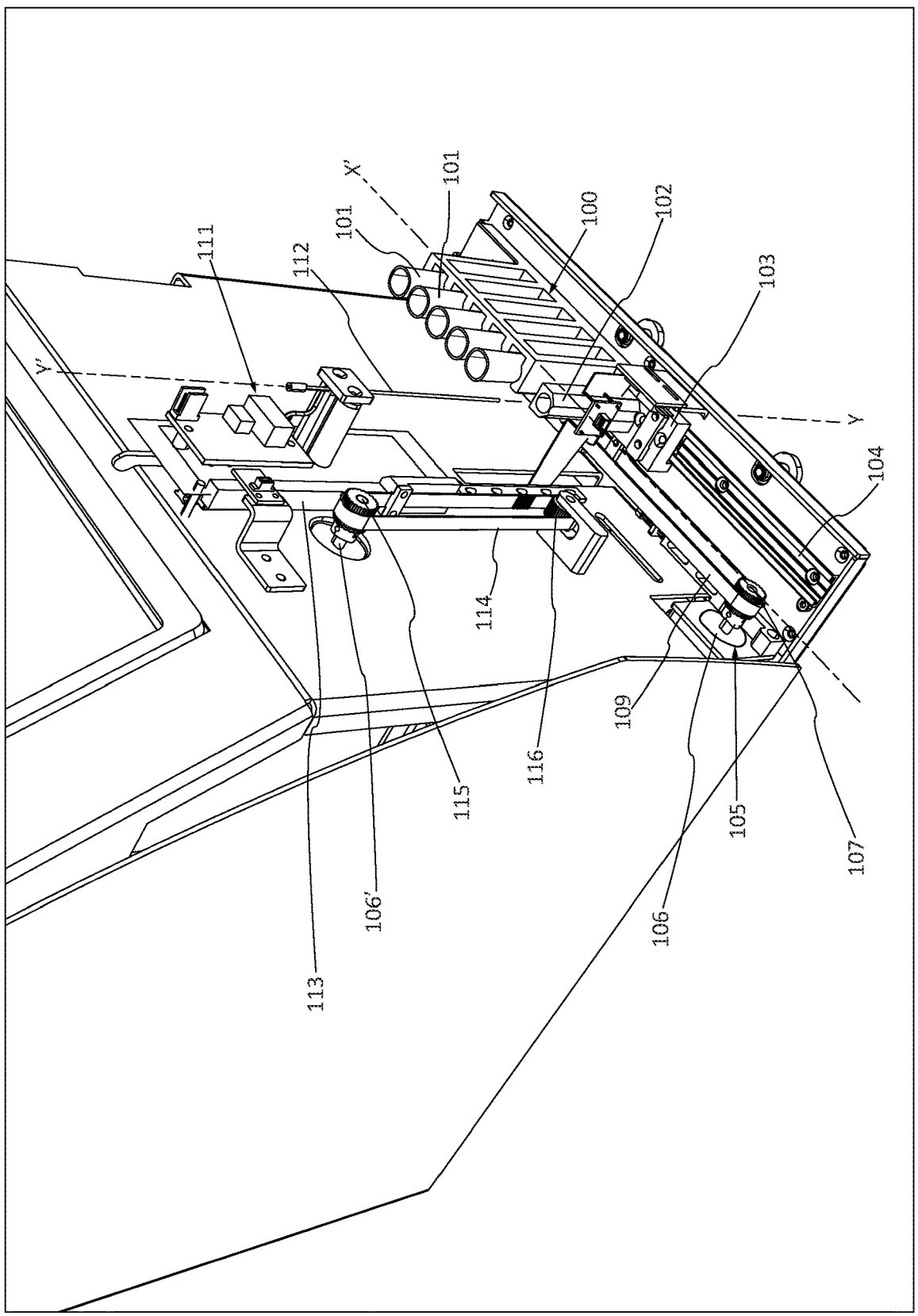
FIG. 4 shows a perspective view from above making it possible to understand the mechanisms of displacement in translation vertically and horizontally.

It is noted that in the embodiment as proposed and illustrated in the drawings, the left electrode, in FIG. 3 for example, is the electrode 201K intended to measure potassium and is always disposed on the left.

On the right side of the rack, and always placed on the right side on the rack, is the reference electrode 202.

The other electrolyte analysis electrodes 201 are interposed, as needed, between the potassium 201K and reference 202 electrodes.

The rack 200 also includes means 203 for pressing the electrodes against each other for the purposes of continuity and sealing as will be explained hereinafter.

These pressing means 203 comprise presses 204 and a clamping screw 205, allowing the presses to be brought closer together.

Figure 5:
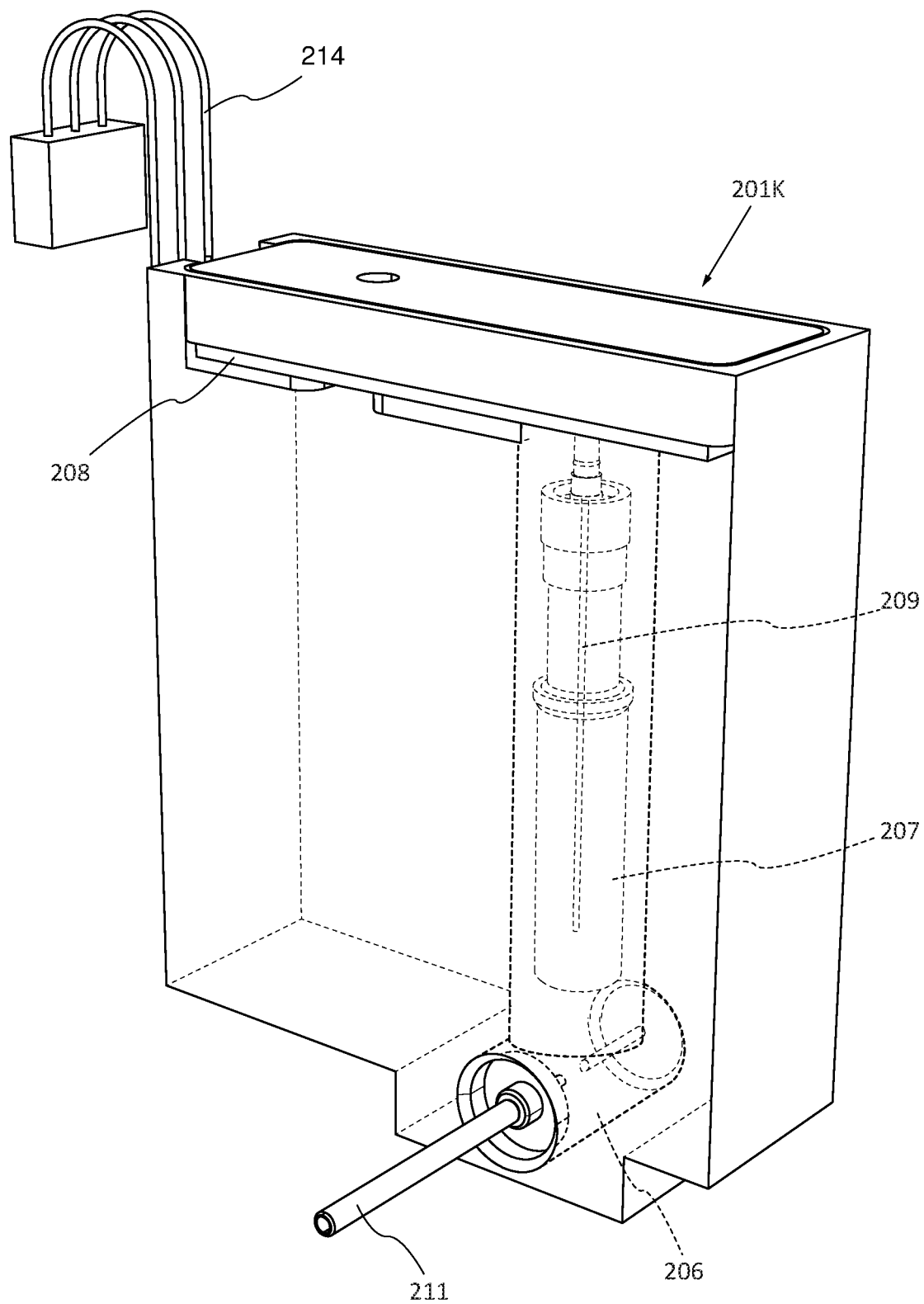
FIG. 5 shows a perspective view of an electrode used in the device according to the present invention.

An electrode according to the present invention is shown in detail in FIG. 5.

This electrode 201, 202 comprises a body with a substantially parallelepiped shape with a through channel 206 at the bottom, a reservoir 207 and an actual electrode 209 opening into the channel, means 208 for storing information relating to the electrode as well as wired connection means 214 intended to connect with the terminals of a terminal block 210. The terminal block 210 is itself connected to the control module 40.

The through channel 206 comprises sealing means between the electrodes at each of its open ends, for example by compression of an O-ring-type seal, so as to provide a seal between two modules and continuous flow from a channel of one electrode to the channel of the following juxtaposed electrode.

The electrode 201K comprises a tap or conduit 211 at its free end, i.e., on the left in the drawing, i.e., the side that cannot be juxtaposed with another electrode.

The reference electrode 202 comprises, symmetrically, a tap 212 on the right.

The pressing means 203 provide the mechanical compression necessary to generate the seal between the electrodes by pressing on the O-rings.

The analysis device according to the invention also optionally incorporates a CO2 measurement cell, 213, independent of the electrode module.

The liquid product reserve module 30 comprises a first container 300 of the reference product used for calibration and, in particular, for rinsing the sampling needle and the channel of the electrode module.

A second container for used fluids 301 is intended to receive the used liquid fluids after the various washing, calibration and analysis operations.

Finally, a third container 302 collects lactic acid intended to supply the cell for measuring the level of CO2 213, when it is present.

The control module 40, comprising electronic and computing means, receives and processes the information coming from the electrodes. A memory storage device integrates a control software program in order to execute the programs for mechanical displacements, circulating fluids, rinsing, reprogramming according to the electrodes in place, calibrations, deep rinses, printing of results or result logs, transmitting information via network connections, sounding alerts if cleaning is needed, if breakdowns cause malfunctions and/or if fluid solution containers need to be replaced.

The fluid connections module 50 comprises the connections between the various containers and members of the device according to the present invention as well as the flow means. The first network 500 connects by a conduit 501 the reference product container 300 to the tap 102P at the bottom of the reference tube 102. A pump 502, for example a peristaltic pump, is interposed on the conduit 501. This pump pulls from the container and feeds the reference tube from below.

The second network 503 comprises a conduit 504 which connects the top of the sampling needle 112 and the tap 211 of the first electrode 201K. The conduit 504 resumes from the tap 212 at the outlet of the reference electrode 202, providing continuity with the inner channel of the juxtaposed electrodes 201.

The conduit 504 opens into the container 301 which collects the used fluids. A pump 505, for example peristaltic, provides the flow in this second network.

If a CO2 measurement cell is present, there is further provided a conduit 506 connecting the third container 302 containing the lactic acid to the CO2 measurement cell 213.

The conduit 504 is then connected to the CO2 measurement cell (not shown) to allow the sample taken with the sampling needle 112 to flow into it at the outlet of the electrolyte-measuring electrodes.

The conduit 504 extends from the CO2 measurement cell to the container 301 that collects the used fluids, and thus the blood sample.

The third network 506 comprises a conduit 507 which connects the third container 302 containing the lactic acid for comparison measurement, a pump, for example peristaltic, providing the flow.

This fluid pattern is simplified for reasons of clarity, but the circuit of the CO2 analysis cell may be more complex in its supply, cleaning and discharge circuits depending on the type of cell, this part not being the subject of the present invention.

The device according to the present invention operates in the manner which is now described, according to basic cycles that may be arranged as required.

First, the device is configured by placing the electrodes necessary for the desired analyses. These electrodes are arranged on the rack 200.

Thus, the electrode 201K (potassium) is placed to the left of the reference electrode 202, which is placed on the right of the rack.

If levels of other electrolytes are to be measured, one need only insert the necessary electrodes between the two electrodes in place, for example two electrodes 201Na (sodium) and 201Ca (calcium). For this, one need only loosen the presses 204 by turning the screw 205. As established in the present embodiment, the reference electrode 202 is stationary and the electrode 201K is moved to the left.

The two additional electrodes 201Na and 201Ca are then inserted.

The wired connection means 214 are connected to the pins of the terminal block 210. The device then recognizes the electrodes added because of the information contained in the memory storage means 208 of each electrode. The control, cycles and measurements will be processed appropriately.

The assembly must then be tightened using the presses 204 by turning the screw 205 in the opposite direction.

This mechanical pressure ensures the pressure on the O-rings between the electrodes and therefore the sealing and the formation of a channel allowing the fluids to flow continuously in the chambers 206.

The samples of liquid of biological origin are placed in the tubes 101, which are positioned in the tube support 100 on the carriage 103.

The reference tube 102 is filled with reference liquid held in the container 300 though its tap 102P at the bottom, by actuating the pump 502.

The program then provides for the sampling needle to pass through the reference tube 102 so as to clean the sampling needle 112.

The sampling needle 112 is lowered by starting up the motor 106', rotating the pulleys 115 and 116 as well as the belt 114.

Reference liquid is then pumped through the sampling needle 112 and passes through the electrodes 201 and 202 in place to provide a start-up calibration on the one hand and a cleaning on the other.

The pump 505 ensures this flow of the reference liquid to the used fluid container 301.

The following cycle comprises raising the sampling needle by vertical translation, providing a translation of the carriage 103 by starting up the motor 105, which drives the pulley 107 and thus the pulley 108 by the toothed belt 109.

The first tube 101 containing liquid of biological origin is positioned in line with the sampling needle 112.

The sampling needle is again lowered so that the end of the needle is in the sample of liquid of biological origin. The pump 505 ensures the flow of the liquid of biological origin through the sampling needle, through the conduit 211, through all the electrodes 201K, 201Na and 201Ca in the case presented, and 202 until it is discharged into the container 301 for used fluids.

The measurements made by the electrodes when the liquid of biological origin passes through the chambers 206 in contact with the actual electrodes 209 are transmitted to the control module 40.

Once the measurements have been made, the circuit is cleaned.

To this end, after raising the sampling needle and removing the tube 101 containing the analyzed liquid of biological origin, the carriage 103 is brought back into position under the sampling needle, which is lowered, and then the reference liquid is drawn in by the needle and flows through the electrodes to end up in the container 301 for collecting used liquid fluids.

The cycle may then be repeated with the contents of the following tube 101, under optimum conditions.

This basic cycle may be completed by conveying the whole blood coming from passing through the electrodes toward the CO2 measurement cell, when this is necessary and when the cell is in place. Used fluids are conveyed into the same container 301.

This CO2 measuring cell, using a commercially available sensor, being more complex in its well-known operation, has a more complex fluid pattern due to the need to introduce lactic acid, wait for the CO2 to develop and measure the pressure increase. For this reason, additional fluid connections must be provided as mentioned above.

This analysis pattern is different, which is why it cannot be coupled directly on the rack with the electrolyte analysis electrodes.

The results with the measurements may be printed if the printer option is provided, and/or they may be transmitted online and/or they may be saved on mass data storage means.

The cycles may be adapted as needed, in particular the cleaning cycles.

With regard to cleaning, a calibration cleaning is provided for each test as described above, but it is also advisable to carry out more aggressive cleaning of the circuit and electrodes every x tests or based on a fixed duration of use or non-use.

A specific calibration is carried out at least once a day to check the sensitivity on the one hand and the response of the electrodes on the other.

According to an improvement of the present invention, the device is equipped with a reference reader, for example a bar code reader, the bar codes being affixed to the sample tubes 101.

The reader being connected to the control module 40, the results for the contents of the tube, identified by a bar code, will be associated with the bar code when it is processed by the sampling needle 112 and consequently, with the sample.

This improvement ensures a perfect correlation between the contents of the tubes 101 and the results obtained, allowing perfect quality control.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A device for analyzing samples of liquid compositions of biological origin, namely whole blood samples for determining electrolytes comprising:
   a frame,
   a sampling module,
   an analysis module comprising electrodes,
   a liquid product reserve module,
   a control module comprising electronic and computing means, and
   a fluid connection network,
   wherein the analysis module comprises a rack configured to hold electrodes for analyzing electrolytes with means for pressing said electrodes against each other to provide continuity and sealing.

2. The device for analyzing samples of liquid compositions of biological origin, namely whole blood samples for determining electrolytes according to claim 1, wherein the sampling module comprises a tube support, containing sample tubes and a reference tube, the tube support being mounted to be movable in translation on a carriage.

3. The device for analyzing samples of liquid compositions of biological origin, namely whole blood samples for determining electrolytes according to claim 2, wherein the carriage is mounted to be movable on guides, connected to a motor, two pulleys, and a toothed belt stretched between said two pulleys.

4. The device for analyzing samples of liquid compositions of biological origin, namely whole blood samples for determining electrolytes according to claim 2, wherein the reference tube comprises a tap at the bottom.

5. The device for analyzing samples of liquid compositions of biological origin, namely whole blood samples for determining electrolytes according to claim 1, further comprising sampling means which comprise a needle carriage on which is disposed a sampling needle with a central channel, the needle carriage being mounted to be movable in translation on guides, the guides being oriented vertically.

6. The device for analyzing samples of liquid compositions of biological origin, namely whole blood samples for determining electrolytes according to claim 1, wherein the rack comprises a stationary reference electrode and a movable potassium electrode, with other electrodes being interposed between these two electrodes.

7. The device for analyzing samples of liquid compositions of biological origin, namely whole blood samples for determining electrolytes according to claim 1, wherein each electrode comprises a body with a through channel in a lower part, an actual electrode opening into said channel, means for storing information relating to said electrode, as well as wired connection means.

8. The device for analyzing samples of liquid compositions of biological origin, namely whole blood samples for determining electrolytes according to claim 7, further comprising a through channel and means for sealing by pressing configured to ensure a continuity of flow from a channel of one electrode to the channel of the following, juxtaposed electrode.

9. The device for analyzing samples of liquid compositions of biological origin, namely whole blood samples for determining electrolytes according to claim 1, wherein the liquid product reserve module comprises a first container for a reference product, a second container for used fluids configured to collect used liquid fluids after various washing, calibration and analysis operations.

10. The device for analyzing samples of liquid compositions of biological origin, namely whole blood samples for determining electrolytes according to claim 1, wherein the liquid product reserve module comprises a third container.

11. The device for analyzing samples of liquid compositions of biological origin according to claim 1, wherein the control module comprises electronic and computing means, a storage device integrating a control software program in order to execute the programs for mechanical displacements, circulating fluids, rinsing, reprogramming according to the electrodes in place, calibrations, deep rinses, printing of results or result logs, transmitting information via network connections, and sounding alerts if at least one of
cleaning is needed,
breakdowns cause malfunctions, and
fluid solution containers need to be replaced.

12. The device for analyzing samples of liquid compositions of biological origin according to claim 1, wherein the device comprises a $CO_2$ analysis module.

13. A method for analyzing samples of liquid compositions of biological origin with the device according to claim 1, comprising adapting the device by arranging the electrodes and performing the following steps:
lowering a sampling needle into a reference tube and pumping a reference liquid so as to clean the sampling needle and perform a calibration,
raising the sampling needle by vertical translation,
positioning a first tube containing a whole blood sample in line with the sampling needle,
lowering the sampling needle so that an end of said needle is in the whole blood sample, causing the blood to flow through the sampling needle, through all the electrodes until discharge into a used fluids container,
taking measurements through the electrodes as whole blood passes through chambers in the device in contact with the electrodes and transmitting to the control module,
positioning the sampling needle in line with the reference tube, lowering said needle, drawing up reference fluid, and circulating the reference fluid through the electrodes to the container for collecting used liquid fluids.

* * * * *